United States Patent
Wuchinich

(10) Patent No.: US 9,962,183 B2
(45) Date of Patent: May 8, 2018

(54) ULTRASONIC TORSIONAL TISSUE DISSECTION UTILIZING SUBALTERN MODES OF LONGITUDINAL-TORSIONAL RESONATORS

(71) Applicant: David Wuchinich, Yonkers, NY (US)

(72) Inventor: David Wuchinich, Yonkers, NY (US)

( * ) Notice: Subject to any disclaimer, the term of this patent is extended or adjusted under 35 U.S.C. 154(b) by 0 days. days.

(21) Appl. No.: 15/206,872

(22) Filed: Jul. 11, 2016

(65) Prior Publication Data

US 2018/0008303 A1    Jan. 11, 2018

(51) Int. Cl.
    *A61B 17/32*    (2006.01)

(52) U.S. Cl.
    CPC ........... *A61B 17/320068* (2013.01); *A61B 2017/320072* (2013.01); *A61B 2017/320084* (2013.01); *A61B 2217/005* (2013.01); *A61B 2217/007* (2013.01)

(58) Field of Classification Search
    CPC ........... A61B 17/320068; A61B 2017/320072; A61B 2217/005; A61B 2017/320096; A61B 2217/007; A61B 2017/320084
    See application file for complete search history.

(56) References Cited

U.S. PATENT DOCUMENTS

| | | |
|---|---|---|
| 4,063,557 A | 12/1977 | Wuchinich et al. |
| 4,233,676 A | 11/1980 | Lücke et al. |
| 4,425,115 A | 1/1984 | Wuchinich |
| 4,493,694 A | 1/1985 | Wuchinich |
| 4,750,488 A | 6/1988 | Wuchinich et al. |
| 4,750,902 A | 6/1988 | Wuchinich et al. |
| 4,922,902 A | 5/1990 | Wuchinich et al. |
| 5,176,677 A | 1/1993 | Wuchinich |
| 5,200,666 A * | 4/1993 | Walter ............ B06B 3/00 310/323.01 |
| 5,811,909 A | 9/1998 | Wuchinich |
| 6,984,220 B2 | 1/2006 | Wuchinich |
| 7,374,552 B2 | 5/2008 | Wuchinich |
| 7,762,552 B2 | 7/2010 | Guerand et al. |
| 8,187,168 B2 | 5/2012 | Wuchinich |
| 8,610,334 B2 | 12/2013 | Bromfield |
| 8,836,200 B2 | 9/2014 | Young et al. |
| 2001/0025184 A1* | 9/2001 | Messerly ....... A61B 17/320092 606/169 |
| 2003/0125620 A1* | 7/2003 | Satou .............. B06B 3/00 600/437 |
| 2012/0293044 A1* | 11/2012 | Bromfield ............ B06B 1/0611 310/323.18 |

OTHER PUBLICATIONS

Frederick, J., Ultrasonic Engineering, John Wiley & Sons, Inc., New York, 1965, pp. 87-100.
"Torsional-Mode Transducers" in Sources of High-Intensity Ultrasound, vol. 2; Rozenberg, L.D., Ed.; Plenum Press, New York, 1969, pp. 135-152.

* cited by examiner

*Primary Examiner* — Richard Louis
(74) *Attorney, Agent, or Firm* — Drinker Biddle & Reath LLP

(57) ABSTRACT

A TL/T tip is made by scaling down the dimensions of an L/T tip by the ratio of the TL/T frequency to the L/T frequency so that the TL/T tip can operate by excitement from a transducer at the same frequency that would have produced L/T motion in the L/T tip. A reductive resonator may be included between the transducer and the TL/T tip.

12 Claims, 3 Drawing Sheets

ULTRASONIC TORSIONAL TISSUE DISSECTION UTILIZING SUBALTERN MODES OF LONGITUDINAL-TORSIONAL RESONATORS

BACKGROUND

Mitskevich (Torsional-Mode Vibration Systems, Sources of High Intensity Ultrasound, Volume 2, Plenum Publishing, NY, 1969, pp. 135-152) disclosed ultrasonic longitudinal-torsional (L/T) resonators in 1967 where their utility in assisting the metal removal action of twist drills was investigated. Wuchinich patented in 2006 (U.S. Pat. No. 6,984,220) such resonators for surgical use in the dissection of hard tissues. Bromfield (U.S. Pat. No. 8,610,334) and Young (U.S. Pat. No. 8,836,200) have subsequently patented longitudinal-torsional ultrasonic transducers for use in surgical operations.

While L/T resonators have proven very useful in assisting the removal of hard tissues such as cortical bone in neurosurgery and orthopedics, they inherently retain a significant encumbrance to their surgical use. Since such resonators produce twisting motion of the tissue excising tip, they contain a component of motion that is longitudinal. Prior art ultrasonic aspirators, used principally for dissection of soft tissue, possess almost entirely longitudinal motion, that is, motion parallel to the longitudinal axis of their slender tips. While this motion induces cavitation of the tissue's intracellular water, thereby rupturing the cell walls and allowing evacuation of their contents and is consummately effective in dissecting soft tissue from low water content tissue such as blood vessels and fascia, this motion also induces cavitation in the irrigation fluid flowing over the tip. Irrigation is essential to the to the operation of such resonators, as the tip must be kept cool and the excised tissue must be lubricated as it is evacuated through the tip to prevent clogging that would otherwise occur from the desiccating effect of the vibration and suction employed to remove the excised tissue through a bore in the tip. Since the motion of L/T tips contains a longitudinal component, these tips also induce cavitation which, however, is not effective in removing hard tissues. It is rather the abrasive effects of the motion possessed by these tips, usually equipped with a burr that is the principal agent of dissection. The unavoidable cavitation mist produced by the longitudinal motion obscures the visual field, preventing precise dissection by the surgeon whose view of the actual surgical site is obstructed.

Torsional resonators are well known in the art and torsional transducers needed to excite such resonators are described at length by Mitskevich as well. In practice, however, designing torsional ultrasonic transducers to power and excite torsional resonators has proved challenging. They are invariably complicated to construct and difficult to incorporate in an appliance that can be facilely manipulated in micro-surgery. But there remains a need for their use where the absence of a longitudinal component of motion sufficient to produce cavitation and mist which blurs vision is a distinct benefit and enhancement.

L/T resonators, however, are excited by longitudinal transducers whose technology is well known in the art and whose design for all manner of applications, including micro-surgical procedures, has been well refined. If longitudinal transducers could be used to excite overwhelmingly torsional motion in a surgical tip, a major advancement in the ultrasonic excision of hard tissue would be achieved.

BRIEF DESCRIPTION OF THE INVENTION

L/T resonators designed for surgical use, where substantial motion is required at the end of tip, possess a resonant mode, aside from their design mode, that is almost wholly torsional. This mode occurs at approximately half the frequency of the L/T mode. For example, an L/T tip designed for operation at 25 kHz also has a lower frequency (subaltern) mode that occurs at approximately 12.5 kHz that produces substantially torsional motion at end of the tip, but also contains at its point of connection to its exciting source, namely an extensional transducer, a longitudinal component, permitting use of a longitudinal transducer to excite this mode. However, as it is usually desirable to use the same transducer for a variety of tips, both longitudinal and L/T, unless a transducer is attached to the tip that has the same subaltern frequency, namely, in this example, 12.5 kHz, the principally torsional mode will not be excited. It is therefore preferable to design the torsional longitudinal-torsional (TL/T) tip to use the same transducer used for other tips, which in this example is 25 kHz.

Because the resonant frequency of both longitudinal and torsional resonators is inversely proportional to the tip length, changing the frequency of a TL/T tip to comport with the transducer amounts to scaling its dimensions, primarily in length and, for L/T resonance, the lateral dimensions as well, by the ratio of the frequency of the TL/T mode to the frequency of L/T mode. In the example cited, this ratio is approximately 0.5. The tip's length and lateral dimensions are halved. Such a shortened tip, however, may be lengthened if necessary by adding one half longitudinal wavelength resonators to the transducer so that these additions become part of the so lengthened tip.

Because the ratio of the longitudinal component of motion of a TL/T tip at the place where it joins the transducer to the torsional component of motion at the end of the tip is much smaller than would be the case if the tip was an L/T tip, the motion of the transducer, which would also be used to excite an L/T tip, must be reduced so that the TL/T tip, where the transducer's motion is communicated to the T/LT tip. Provision must be made such that the TL/T is not excited beyond its safe limits of vibrational endurance. However, since the useful power available from the transducer is proportional to the square of the transducer's motion itself, simply lowering the motion of the transducer by reducing its electrical driving voltage and current will not provide enough power to the TL/T tip to perform useful work. The addition of a reductive longitudinal resonator, interposed between the transducer and tip, however, not only lengthens the tip as just described but also permits the transducer itself to produce the same motion necessary for exciting an L/T tip while reducing the motion to the requisite level at the connection of the reductive resonator to the TL/T tip, thereby making available the full output power of the transducer for dissection when using a TL/T tip.

In summary, this invention prescribes a method for designing L/T resonators such that they execute the subaltern TL/T mode resonance of torsional tissue dissecting vibration while operating at the same frequency as an L/T resonator and provides for incorporation of a device, the reductive resonator, for permitting the use of the same transducer used to excite the L/T resonator for excitation and operation of a TL/T tip operating within its safe limits of vibration.

Reference numerals in the drawings

Figure 1:
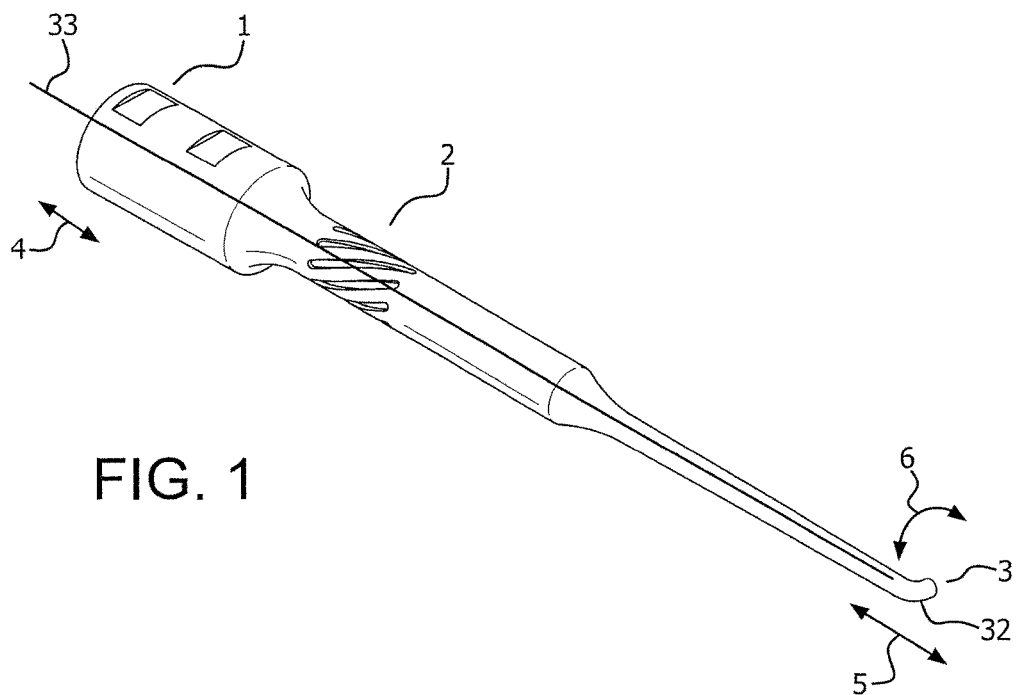
FIG. 1 illustrates an L/T ultrasonic tip executing L/T motion.

| Item | Description |
|---|---|
| 1 | Face of L/T tip for receiving extensional motion from transducer. |
| 2 | Spiral grooves for generating L/T motion. |
| 3 | Tissue dissecting terminus of L/T tip. |
| 4 | Direction and relative magnitude of motion at receiving face of L/T tip executing L/T motion. |
| 5 | Direction and relative magnitude of extensional component of motion of terminus executing L/T motion. |
| 6 | Direction and relative magnitude of torsional component of motion of terminus executing L/T motion. |
| 7 | Direction and relative magnitude of motion of receiving face of TL/T tip executing torsional motion. |
| 8 | Direction and relative magnitude of extensional component of motion of tissue dissecting terminus of TL/T tip. |
| 9 | Direction and relative magnitude of torsional component of motion of tissue dissecting terminus of a TL/T tip. |
| 10 | Face of an L/T tip for receiving extension motion from a transducer. |
| 11 | Twisted surface of L/T tip for generating L/T motion. |
| 12 | Tissue dissecting terminus of L/T tip. |
| 13 | Ultrasonic transducer for generating extensional motion. |
| 14 | Reductive extensional resonator for reducing motion received from transducer. |
| 15 | TL/T tip. |
| 16 | Piezo-active element of transducer. |
| 17 | Spindle section of reductive resonator. |
| 18 | Communicating section of reductive resonator. |
| 19 | First material section of reductive resonator. |
| 20 | Second material section reductive resonator. |
| 21 | Reductive resonator composed of disparate materials. |
| 22 | Reductive resonator having a uniform outer diameter. |
| 23 | First section of reductive resonator. |
| 24 | Cross section of second section of reductive resonator. |
| 25 | Second section of reductive resonator. |
| 26 | Cross section of aspirator conduit fitted to reductive resonator. |
| 27 | Cross section of first section of reductive resonator. |
| 28 | Direction and relative magnitude of motion received from transducer by reductive resonator using disparate materials. |
| 29 | Direction and relative magnitude of motion imparted by reductive resonator using disparate materials to TL/T tip. |
| 30 | Direction and relative magnitude of motion received by a reductive resonator of uniform diameter from extensional transducer. |
| 31 | Direction and relative magnitude of motion imparted by a reductive resonator of uniform diameter to a TL/T tip. |
| 32 | Passage way for aspiration within tip. |
| 33 | Longitudinal axis of tip. |
| 34 | Direction and magnitude of transducer exciting extensional motion. |
| 35 | Direction and magnitude of reductive resonator tip exciting extensional motion. |
| 36 | Direction and magnitude tip terminus torsional motion. |
| 38 | Receiving face, disparate material reductive resonator. |
| 39 | Exciting face, disparate material reductive resonator. |
| 40 | Receiving face of reductive resonator having different cross sectional areas. |
| 41 | Exciting face of reductive resonator having different cross sectional areas. |
| 42 | Electrical connections to piezo-active element in transducer. |
| 43 | Joint of disparate materials in reductive resonator. | quently generates two motions, an extensional motion 5 and a rotational motion 6 at its tissue dissecting terminus 3. In general the magnitude of the two motions 5 and 6 are comparable so that the movement of a point on the terminus appears to execute a motion at an angle to the tip's longitudinal axis 33. This angle, determined by the relative magnitudes of the motion and by the tip's design can vary from as little as ten to as much as seventy degrees or more. In practice it is generally desirable that the angle be in the range of 30 to 60 degrees for efficacious dissection of cortical bone. An important consideration is the ratio of the magnitude of the motion of the terminus, the combined extensional and rotational motion, to that 4 at the receiving face. This ratio is termed the gain of the tip. As the receiving face motion is that produced by the transducer, the gain of the tip determines the magnitude of motion of the terminus, which must be kept with the safe limits of endurance of the material from which the tip is made.

DETAILED DESCRIPTION OF THE INVENTION

Figure 2:
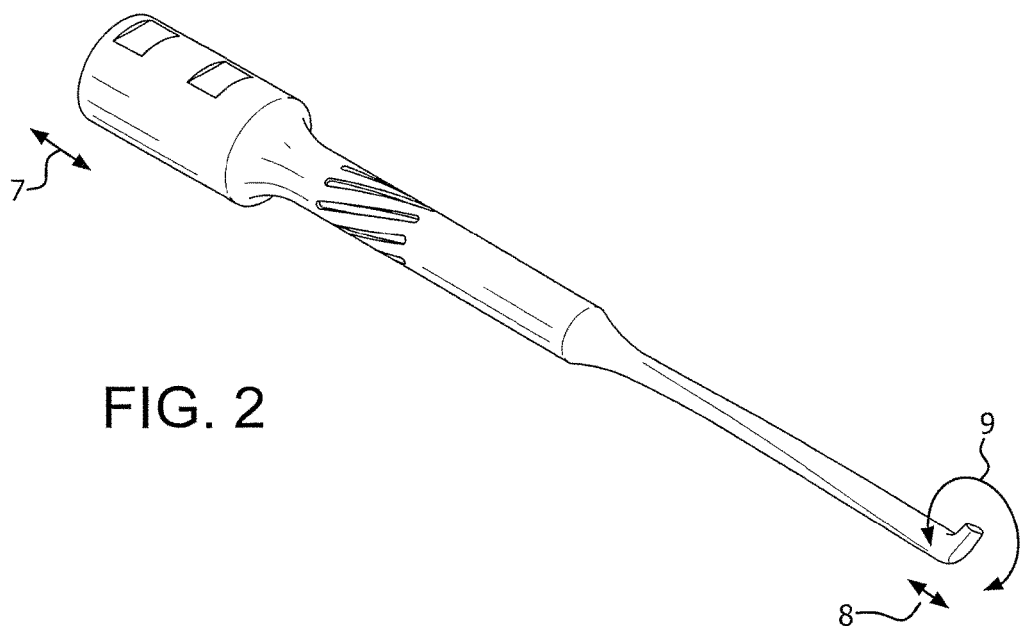
FIG. 2 shows an L/T ultrasonic tip performing torsional motion.

FIG. 1 depicts an L/T tip of conventional design operating at resonance in its design L/T mode. A tip comprises a resonator and its tissue dissecting terminus. Spiral grooves 2 in the surface of part of the tip generate longitudinal-torsional motion in the structure when the tip is excited by an extensional motion 4 at its receiving face 1. It conse- FIG. 2 depicts the same tip shown in FIG. 1 but operating in the subaltern resonant mode known as the torsional longitudinal-torsional (TL/T) mode. In general the frequency of the subaltern mode is approximately half that of the L/T mode. In this mode, an exciting extensional motion 7 at its receiving face results in an extensional motion 8 of the terminus of much smaller magnitude, for the same exciting motion, than is the case for operation in the L/T mode. However, the rotational component of motion 9 is much larger, for the same longitudinal exciting motion, than prevails in the L/T mode. As a result the motion of the terminus is almost entirely torsional and the motion of a point on the terminus appears to execute a motion almost perpendicular to the axis of the tip. Thus, imparting an extensional motion at the frequency of the subaltern mode from the transducer generates an almost wholly torsional motion at the tissue dissecting terminus, a desirable effect since the absence of an appreciable longitudinal component of motion prevents cavitation of irrigating fluid, a fluid which is always present during a surgical procedure, from obscuring the field of vision thereby permitting precise dissection.

The gain of a tip resonating in TL/T mode is much larger than that of the tip resonating in the L/T mode. As a result, if the same motion produced by a transducer exciting the L/T mode is applied to a tip executing the TL/T mode, motion of the terminus may become sufficiently large to cause destruction of the tip.

The tip shown in FIGS. 1 and 2 may also contain a passage 32 running the length of the tip for the evacuation of dissected tissue. This passageway is usually connected to a source of vacuum in the rest of the instrument and removes both tissue and irrigation fluid during the procedure.

Figure 3:
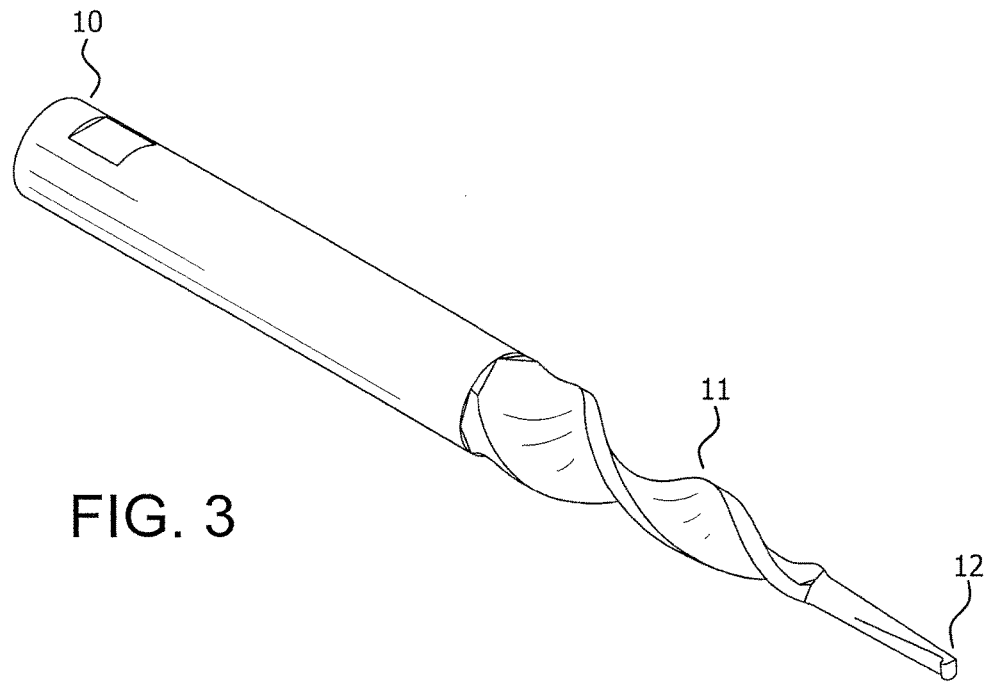
FIG. 3 is a rendering of another form of L/T tip.

FIG. 3 illustrates another embodiment of an L/T tip with the face for receiving exciting motion 10 and a terminus 12 for tissue dissection. L/T motion is generated by the spiral twist 11 of an intermediate portion. The embodiment of FIG. 3 is based on U.S. Pat. No. 6,984,220 and U.S. Pat. No. 7,374,552, all of the details of which are incorporated herein by reference thereto. This tip also possesses a subaltern mode whose resonant frequency is approximately half that of the L/T resonant frequency.

Because the resonant frequencies of the L/T and subaltern (TL/T) modes differ substantially in frequency, the transducer, which excites their motion and which must also be resonant at the frequency of the mode of interest, cannot be used to excite both modes. Either separate transducers must be attached, having the correct resonant frequencies, or the tip must be designed, if TL/T mode operation is desired, to have same resonant frequency as the L/T tip. Having to use separate transducers for each tip, L/T and TL/T, is a distinct disadvantage to surgical use as it requires two separate assemblies, transducer and tip and associated support accessories when various occasions require the alternate use of both. Separate transducers also increase the cost of the equipment to the user and thus suffer a commercial disadvantage to the manufacturer whose cost to user is burdened by having to offer two separate appliances.

As both longitudinal and torsional resonances are inversely proportional to length, a TL/T tip can be designed from an L/T tip by scaling its length by the ratio of the subaltern mode frequency to the L/T frequency. Because scaling just the length alters the pitch of the grooves 2 preserving the pitch requires that the lateral dimensions also be scaled by the same factor. Every part of the resonator, including the terminus is scaled down. A tip, so scaled, will then have a TL/T mode of the same frequency as the transducer used to excite the L/T mode. A suitable ratio (torsional/longitudinal motion) for an L/T top ranges from 0.5 to 2. The range for a TL/T tip is 5 to 20. The preferred range is 10 to 15.

This aspect of the invention thus involves starting with an L/T tip as a standard or basis of comparison. Such L/T tip could be an actual tip or the physical (dimensional) specifications for an L/T tip. The dimensions of the comparison L/T tip are then scaled down in length and preferably also lateral dimensions by a ratio of the subaltern frequency to the L/T frequency to result in an instrument having a TL/T tip operated by the transducer at the same frequency which would have produced L/T motion in the comparison tip.

However, although equality in resonant frequencies between the extensional transducer and TL/T tip can be so obtained, if the exciting levels of motion of the transducer used for an L/T tip are applied to the TL/T tip, very large torsional motions of the tip's terminus are produced that may result in failure of the tip itself. The electrical voltage, V, and current, I, shown in FIG. 4 powering the transducer can be adjusted to reduce the exciting motion, but at a sacrifice of deliverable dissection power. The power available from a transducer is proportional to the square of its exciting motion. If the exciting motion needed for safe operation of a TL/T tip is one half of that required for an L/T tip, the available power for tissue dissection using the TL/T tip is one quarter of that available for L/T dissection. Hence, it is desirable, if full dissection power is to be made available for use with a TL/T tip, to reduce the exciting motion to the tip without reducing the exciting motion of the transducer.

Figure 4:
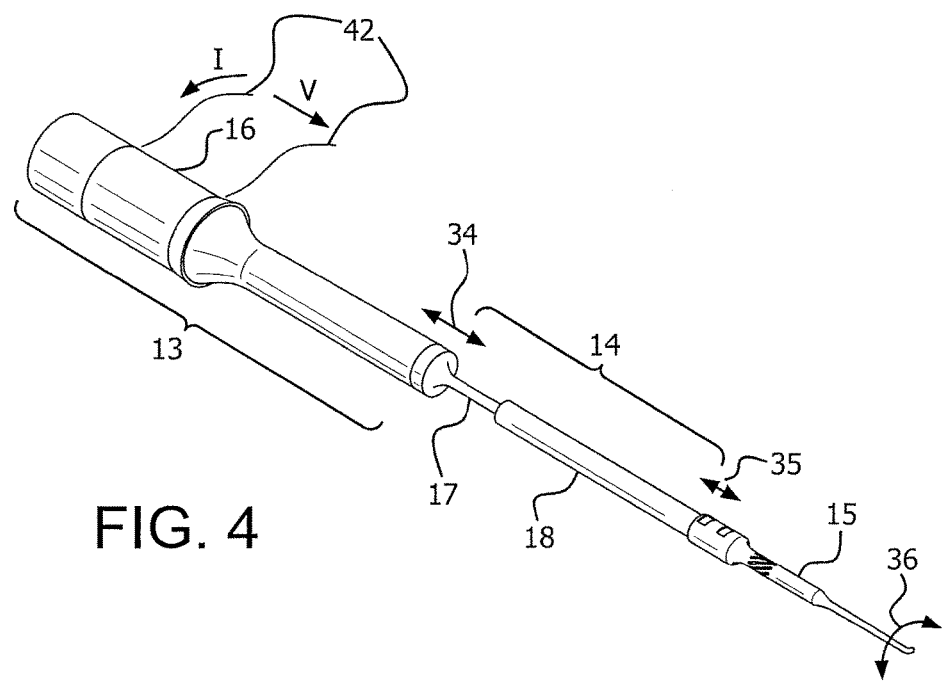
FIG. 4 depicts the connection of a transducer suitable for powering a conventional L/T in L/T motion to a reductive extensional resonator connected to an L/T tip for providing torsional motion.

FIG. 4 provides an embodiment of the invention. Extensional transducer 13 containing piezo-active element 16 with connections 42 to a source of electrical energy, is joined to extensional reductive resonator 14 that, in turn, is joined to scaled down TL/T tip 15. The reductive resonator 14 is composed to two sections. The transducer, reductive resonator and tip are all resonant at the same frequency. Section 17 is the spindle section which has a reduced diameter and section 18 is the communicating section which has an enlarged diameter.

In operation, the transducer produces an exciting extensional motion 34 that is communicated to the reductive resonator 14 which, in turn, produces a diminished extensional motion 35 that excites tip 15 and results in torsional motion 36 at the terminus of the tip.

Reductive resonators act acoustically as step-down motional transformers. They do not diminish the motion by attenuation and ideally consume no power, conveying the power received at their receiving face to an identical power at their opposite face, which in FIG. 4 is communicated to the tip. Such resonators can have many forms and are known as horns in the art. Stepped, exponential, catenoidal, conical, Gaussian and other geometries are known to acousticians. Reductive resonator 14 shown in FIG. 4 is a particularly simple construction. In general, the motion at the receiving face is related to the motion at the opposite face by a factor, C, where C is a trigonometric function of the lengths of sections 17 and 18 and the ratio of their cross sectional areas.

The addition of the reductive resonator 14 permits the transducer to be operated at levels adequate to excite an L/T tip while reducing the level of excitation provided to the TL/T tip. In this construction, during a procedure, should L/T tissue dissection be desired, reductive resonator 14 and TL/T tip 15 can be removed from the transducer 13 and replaced with an L/T tip, obviating the need for an additional transducer, an important convenience in surgical procedures and an economy in use.

Figure 5:
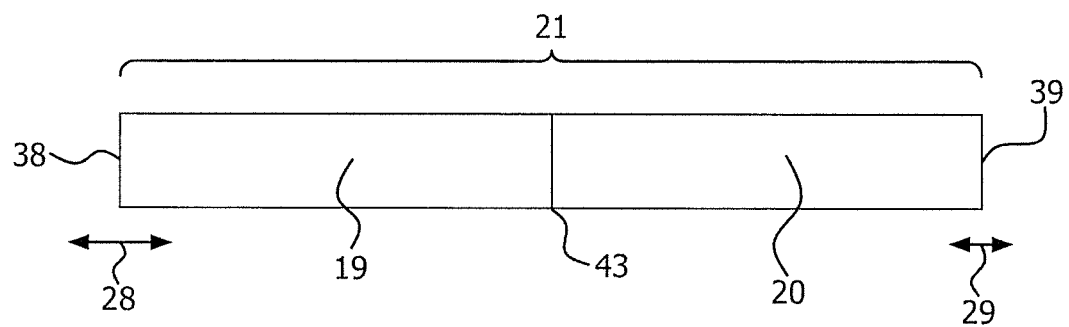
FIG. 5 shows another form of a reductive extensional resonator using disparate materials.

If a uniform outer surface of the reductive resonator is desired, one not having a transition in diameter, for example, FIG. 5 illustrates a reductive resonator 21 composed of two different materials. The motion 28 of receiving face 38 is reduced 29 at exciting face 39 through the use of two different materials 19 and 20 joined together. The Gain, C, of such a resonator is, as before, a trigonometric function of the lengths of sections made of materials 19 and 20 as well as the ratio of the cross sectional area of section of material 19 to that of material 20. But, in addition, as is well known in acoustic design, the gain C is also a function of the ratio of the acoustic impedance of material 19 to the acoustic impedance of material 20. The acoustic impedance is defined as the product of the material's density and its extensional sound velocity.

If, for example, material 19 is aluminum and material 20 is tungsten, even though both materials have the same diameter, the resonator will act to reduce the motion at receiving face 38. Alternatively, if material 19 is titanium and material 20 is stainless steel, the motion will also be reduced. In practice the joint 43 of the two materials made by made using a threaded attachment or by metallurgical joining, such as welding brazing. Other combinations of materials are possible, all resulting in a reduction of motion.

Figure 6:
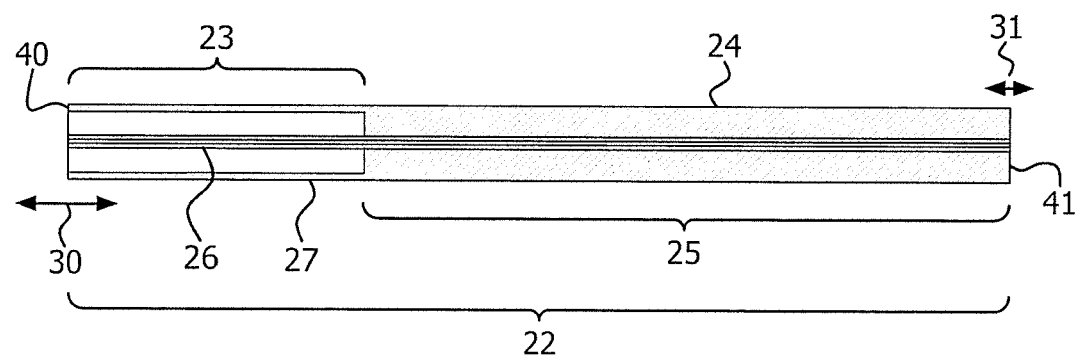
FIG. 6 provides another form of a reductive extensional resonator using varying cross sectional areas.

Another method of providing a uniform outer surface for a reductive resonator 22 composed of one material is shown in FIG. 6 which provides a cross section view of a symmetric construction. Section 23 has a smaller cross sectional area 27 than the area 24 of section 25 with the result that the motion 30 of the receiving face 40 is reduced 31 at the exciting face.

FIG. 6 also shows provision for the incorporation of an aspiration passage 26 through both sections of the resonator, permitting removal of irrigation fluid and dissected tissue. By adjusting the lengths of sections 23 and 25, the Gain, C, of this resonator can be adjusted from a value of unity to a minimum value equal to the ratio of the cross sectional area 27 of section 23 to the cross section area 24 of section 25.

Many other variations of reductive resonators are possible and are well known in the art. Such resonators may be made integral with the TL/T tip or be separately attached to the tip using any one of the conventional methods: screw joints, press-fitting, welding or brazing. The releasable attachment of the reductive resonator to the transducer can be made using screw threads or other releasable joining method.

What is claimed is:

1. In a method of forming an ultrasonic tissue dissection instrument which includes a transducer connected to a tip having a resonator for producing exciting extensional motion in the resonator and producing motion in the terminus of the tip, the improvement being in selecting as a comparison tip a tip which is capable of producing L/T motion when operated by a transducer at a specified frequency and capable of being operated in a subaltern mode when operated by a transducer at a frequency substantially lower than the specified frequency, forming an TL/T tip by using for the length and lateral dimensions reduced dimensions which are scaled down from the length and lateral dimensions of the comparison tip by a ratio of the subaltern frequency to the L/T frequency, and creating TL/T motion in the TL/T tip by operating the transducer at the same specified frequency which would have produced L/T motion in the comparison tip.

2. The method of claim 1 wherein the instrument is lengthened by adding one half longitudinal wavelength resonators to the transducer.

3. The method of claim 1 wherein the reduced dimensions are scaled down by 0.5.

4. The method of claim 1 including inserting a reductive resonator between the transducer and the TL/T tip.

5. In a method of forming an ultrasonic tissue dissection instrument which includes a transducer connected to a tip having a resonator and a tissue dissection terminus whereby extensional motion is excited by the transducer and motion is produced at the terminus, the improvement being in inserting as the resonator a reductive resonator between the transducer and the tip, the reductive resonator and the tip being resonant at the same frequency as the frequency of the transducer, the tip being a TL/T tip, and the TL/T tip is produced by the method of claim 1.

6. In a method of forming an ultrasonic tissue dissection instrument which includes a transducer connected to a tip having a resonator and a tissue dissection terminus whereby extensional motion is excited by the transducer and motion is produced at the terminus, the improvement being in inserting as the resonator a reductive resonator between the transducer and the tip, the reductive resonator and the tip being resonant at the same frequency as the frequency of the transducer, the tip being a TL/T tip, the transducer producing an exciting extensional motion communicated to the reductive resonator, and the reductive resonator producing a diminished extensional motion that excites the TL/T tip and results in torsional motion at the terminus of the TL/T tip.

7. The method of claim 6 wherein the reductive resonator which is used includes a reduced diameter section joined to an enlarged diameter section joined to the TL/T tip.

8. The method of claim 6 wherein the reductive resonator and the TL/T tip are removably mounted to the transducer whereby the reductive resonator and the TL/T tip may be replaced with an L/T tip.

9. The method of claim 8 including removing the reductive resonator and the TL/T tip from the transducer, and mounting an L/T tip to the transducer.

10. The method of claim 6 wherein the reductive resonator which is used has a uniform outer surface and is composed of two different materials longitudinally aligned with each other.

11. The method of claim 6 wherein the reductive resonator which is used has a uniform outer surface and is composed of a first section longitudinally aligned with a second section, and the first section having a smaller cross sectional area of material than the second section.

12. The method of claim 11 wherein the first section is adjacent to the transducer, and the second section being adjacent to the TL/T tip.

* * * * *